United States Patent
Kobayashi et al.

(10) Patent No.: US 7,256,316 B2
(45) Date of Patent: ***Aug. 14, 2007

(54) FLUORINE-CONTAINING VINYL ETHERS, THEIR POLYMERS, AND RESIST COMPOSITIONS USING SUCH POLYMERS

(75) Inventors: Satoru Kobayashi, Saitama (JP); Kazuhiko Maeda, Tokyo (JP); Tooru Tsujishita, Saitama (JP)

(73) Assignee: Central Glass Company, Limited, Ube-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/533,788

(22) PCT Filed: Oct. 30, 2003

(86) PCT No.: PCT/JP03/13924

§ 371 (c)(1),
(2), (4) Date: May 4, 2005

(87) PCT Pub. No.: WO2004/041762

PCT Pub. Date: May 21, 2004

(65) Prior Publication Data

US 2006/0074263 A1 Apr. 6, 2006

(30) Foreign Application Priority Data

Nov. 5, 2002 (JP) ............................. 2002-320871
Jan. 31, 2003 (JP) ............................. 2003-022925

(51) Int. Cl.
*C07C 43/18* (2006.01)
*C07C 43/02* (2006.01)

(52) U.S. Cl. ...................... 568/665; 568/669; 568/655; 568/656; 526/318; 430/270.1

(58) Field of Classification Search ................ 568/665, 568/669, 655, 656; 526/318; 430/270.1
See application file for complete search history.

(56) References Cited

U.S. PATENT DOCUMENTS

| | | | |
|---|---|---|---|
| 3,371,064 A | 2/1968 | Wall et al. .................. | 526/247 |
| 3,488,335 A | 1/1970 | Braun et al. ................. | 526/247 |
| 3,529,003 A | 9/1970 | Rausch et al. .............. | 556/448 |
| 3,752,789 A | 8/1973 | Khan et al. .................. | 528/488 |
| 6,858,760 B2 * | 2/2005 | Komoriya et al. .......... | 568/820 |
| 2003/0219679 A1 | 11/2003 | Sasaki et al. ............. | 430/270.1 |
| 2003/0232277 A1 | 12/2003 | Sasaki et al. ............. | 430/270.1 |
| 2003/0236369 A1 | 12/2003 | Komoriya et al. .......... | 526/248 |
| 2004/0214102 A1 * | 10/2004 | DiPietro et al. ......... | 430/270.1 |

FOREIGN PATENT DOCUMENTS

| | | |
|---|---|---|
| EP | 536690 | 4/1993 |
| JP | 2002-201231 | 7/2002 |
| JP | 2003-316004 | 11/2003 |
| JP | 2003-327686 | 11/2003 |
| WO | 95/20021 | 7/1995 |
| WO | 02/36646 | 5/2002 |

OTHER PUBLICATIONS

An article by Y. Kamon et al entitled, "Newly Developed Acrylic Copolymers for ArF Photoresist", Journal of Photopolymer Science and Technology vol. 15, No. 4 (Jun. 2002) 535-540.
An article by Robert McClelland et al entitled, "Mechanism of Hydrolysis of Aryl Vinyl Selenides, Selenium-Stabilized Carbonium Ions", J. Org. Chem. Jan. 1980, 45, 187-189.
An article by Ernst Eibler et al entitled, Polyhalogenated Cyclopentadienes in [4+2] Cycloadditions: Preparative Aspects, Liebigs Ann./Recueil *1997, 2451-2469.
An article by Raymond G. Plevey et al entitled, "Polyfluorocycloalkenes, Part XVII, Further Preparations of Alkoxy-Nonafluorocyclohexenes and their Pyrolyses to Polyfluorocyclohex-2-Enones", Journal of Fluorine Chemistry, 26 (Dec. 1984) 515-531.

* cited by examiner

*Primary Examiner*—Rosalynd Keys
(74) *Attorney, Agent, or Firm*—Crowell & Moring LLP

(57) ABSTRACT

A fluorine-containing vinyl ether represented by formula 1, $$H_2C = \!\!\!\!\!\!\!\!\!\!\!\!\!\!\!\!\!\!\!\!\!\!\!\!\!\!\!\!\!\! \diagdown_{O-R} \quad (1)$$

wherein R represents an organic group containing at least one fluorine atom and a cyclic structure is provided. A fluorine-containing copolymer containing (a) a first unit derived from a first monomer that is a fluorine-containing vinyl ether represented by formula 8:

(8)

where $R^1$ is —H or a $C_1$-$C_8$ alkyl group that optionally contains an oxygen atom; and (b) a second unit derived from a second monomer that is at least one selected from acrylic esters and methacrylic esters is also provided.

19 Claims, No Drawings

FLUORINE-CONTAINING VINYL ETHERS, THEIR POLYMERS, AND RESIST COMPOSITIONS USING SUCH POLYMERS

BACKGROUND OF THE INVENTION

The present invention relates to fluorine-containing vinyl ethers, their polymers and copolymers, and resist compositions using such polymers and copolymers.

Hitherto, fluorine-containing polymers have been used in various fields, since they are superior in heat resistance and chemical resistance. In particular, amorphous fluorine-containing polymers are further superior in transparency, and therefore they have been used and studied in the fields of optical fiber and resist composition (see Japanese Patent Application Publication 2002-201231). In fact, the introduction of fluorine atoms lowers refractive index or improves transparency of the vacuum ultraviolet region light.

In the development of resist compositions (see Y. Kamon et al., J. Photopolym. Sci. Technol., 15, 535 (2002)), now, a major resist type is a positive-type resist composition, in which an acid is generated by light irradiation and then solubility of a resin of the resist composition in alkali aqueous solution changes due to a chemical change of the resin by an action of the acid as a catalyst. In the trend toward shorter wavelength light source to manufacture smaller semiconductor devices, there are problems that resins (e.g., novolak resins and acrylic resins) used in current resists are insufficient in transparency. Thus, there are a demand for polymers that contain fluorine atoms, do not contain structures such as carbonyl, and are superior in heat resistance and solubility in various solvents, and a demand for monomers for synthesizing such polymers.

Recent research and development have revealed that acrylic resins have a possibility to have relatively good resist characteristics (see Y. Kamon et al., J. Photopolym. Sci. Technol., 15, 535 (2002)). Acrylic resins, however, contain carbonyl structures that absorb vacuum ultraviolet light. Therefore, they are still not sufficient in transparency and are required to achieve further improvement.

Since conventional fluorine-containing monomers are inferior in copolymerizability with acrylic or methacrylic esters, it has been difficult to copolymerize acrylic monomers with fluorine-containing monomers. Thus, there are a demand for fluorine-containing monomers that do not have carbonyl structures and are superior in copolymerizability with acrylic or methacrylic monomers and a demand for copolymers of such fluorine-containing monomers and acrylic or methacrylic monomers.

SUMMARY OF THE INVENTION

It is therefore an object of the present invention to provide (a) monomers that can be a raw material for producing polymers, which are low in light scattering and absorption and high in transparency, (b) such polymers, and (c) resist compositions using such polymers.

It is another object of the present invention to provide (a) fluorine-containing copolymers that are low in light scattering and absorption and high in transparency and (b) resist compositions using such copolymers.

According to a first aspect of the present invention, there is provided a fluorine-containing vinyl ether represented by the formula 1, $$H_2C=\!\!\!=\!\!\!\diagdown_{O-R} \quad (1)$$

wherein R represents an organic group comprising at least one fluorine atom and a cyclic structure.

The organic group (R) of the formula 1 may comprise:

(a) the cyclic structure that is selected from the group consisting of cyclopentane ring, cyclohexane ring, norbornene ring, aromatic rings, tricyclodecane ring; and (b) at least one substituent that is selected from the group consisting of $(-OH)_m$, $(-R^1)_n$, and $-COOR^4$ where $R^1$ is at least one substituent selected from the group consisting of $-F$, $-CF_3$, and $-R^2C(CF_3)_2OR^3$, where $R^2$ is $CH_2$ or $C_2H_4$, and $R^3$ is H or an acid-labile protecting group, $R^4$ is H, a $C_1$-$C_{15}$ alkyl group, or a $C_1$-$C_{15}$ substituent containing an ether bond, and m is 0 or 1, and n is an integer of 1-8.

The fluorine-containing vinyl ether of the formula 1 may be represented by the formula 2, $$(2)$$

$H_2C=\!\!\!=\!\!\!\diagdown_{O}$ — (cyclohexane ring with $(HO)_m$ and $(R^1)_p$ substituents)

where $R^1$ is at least one substituent selected from the group consisting of $-F$, $-CF_3$, and $-R^2C(CF_3)_2OR^3$, where $R^2$ is $CH_2$ or $C_2H_4$, and $R^3$ is H or an acid-labile protecting group, and p is an integer of 1-5, and m is 0 or 1.

The fluorine-containing vinyl ether of the formula 1 may be represented by the formula 3, $$(3)$$

$H_2C=\!\!\!=\!\!\!\diagdown_{O}$ — (norbornane ring with $(HO)_m$ and $(R^1)_q$ substituents)

where $R^1$ is at least one substituent selected from the group consisting of $-F$, $-CF_3$, and $-R^2C(CF_3)_2OR^3$, where $R^2$ is $CH_2$ or $C_2H_4$, and $R^3$ is H or an acid-labile protecting group, and q is an integer of 1-4, and m is 0 or 1.

The fluorine-containing vinyl ether of the formula 1 may be represented by the formula 4, $$(4)$$

$H_2C=\!\!\!=\!\!\!\diagdown_{O}$ — (aromatic ring with $(HO)_m$ and $(R^1)_p$ substituents)

where $R^1$ is at least one substituent selected from the group consisting of $-F$, $-CF_3$, and $-R^2C(CF_3)_2OR^3$, where $R^2$ is $CH_2$ or $C_2H_4$, and $R^3$ is H or an acid-labile protecting group, and p is an integer of 1-5, and m is 0 or 1.

The fluorine-containing vinyl ether of the formula 1 may be represented by the formula 5,

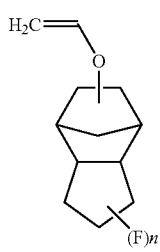

(5)

where n is an integer of 1-8.

The fluorine-containing vinyl ether of the formula 1 may be represented by the formula 6,

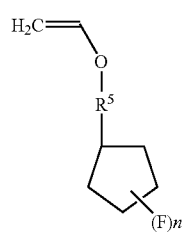

(6)

where $R^5$ is a $C_0$-$C_5$ alkyl group, and n is an integer of 1-8.

The fluorine-containing vinyl ether of the formula 1 may comprise a hexafluoroisopropanol unit represented by the formula 7,

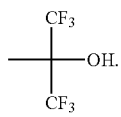

(7)

According to the first aspect of the present invention, there are provided (a) a fluorine-containing polymer comprising a unit derived from the fluorine-containing vinyl ether of the formula 1, and (b) a resist composition comprising this fluorine-containing polymer.

According to a second aspect of the present invention, there is provided a fluorine-containing copolymer comprising:

a first unit derived from a first monomer that is a fluorine-containing vinyl ether represented by the formula 8:

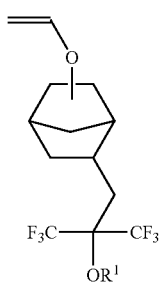

(8)

where $R^1$ is —H or a $C_1$-$C_8$ alkyl group that optionally contains an oxygen atom; and a second unit derived from a second monomer that is at least one selected from the group consisting of acrylic esters and methacrylic esters.

The second monomer may be a first methacrylic ester represented by the following formula 9.

The second monomer may be an acrylic or methacrylic ester comprising a lactone ring.

The second monomer may be a second methacrylic ester represented by the following formula 10.

A fluorine-containing copolymer according to the second aspect of the present invention may comprise:

a first unit derived from a first monomer that is a fluorine-containing vinyl ether represented by the formula 11; and a second unit derived from a second monomer that is a combination of first and second methacrylic esters represented by the formulas 9 and 10,

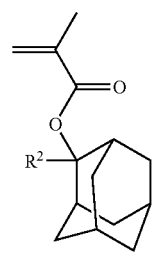

(9)

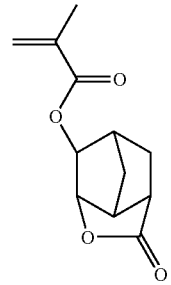

(10)

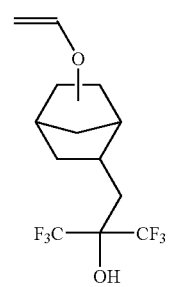

(11)

where $R^2$ is —$CH_3$ or —$CH_2CH_3$.

According to the present invention, there is provided a resist composition comprising a fluorine-containing copolymer of the second aspect of the present invention.

DESCRIPTION OF THE PREFERRED EMBODIMENTS

The first aspect of the present invention is described in detail, as follows. The inventors unexpectedly found that a novel fluorine-containing vinyl ether according to the first aspect of the present invention is free from the above-mentioned conventional problems. Specifically, it was found that the fluorine-containing vinyl ether is capable of producing homopolymers and copolymerizing with various monomers, and that the resulting fluorine-containing polymers dissolve in various organic solvents and have high transparency. Therefore, they are useful as transparent resist compositions.

Specific examples of the fluorine-containing vinyl ether include those represented by the following structural formulas:

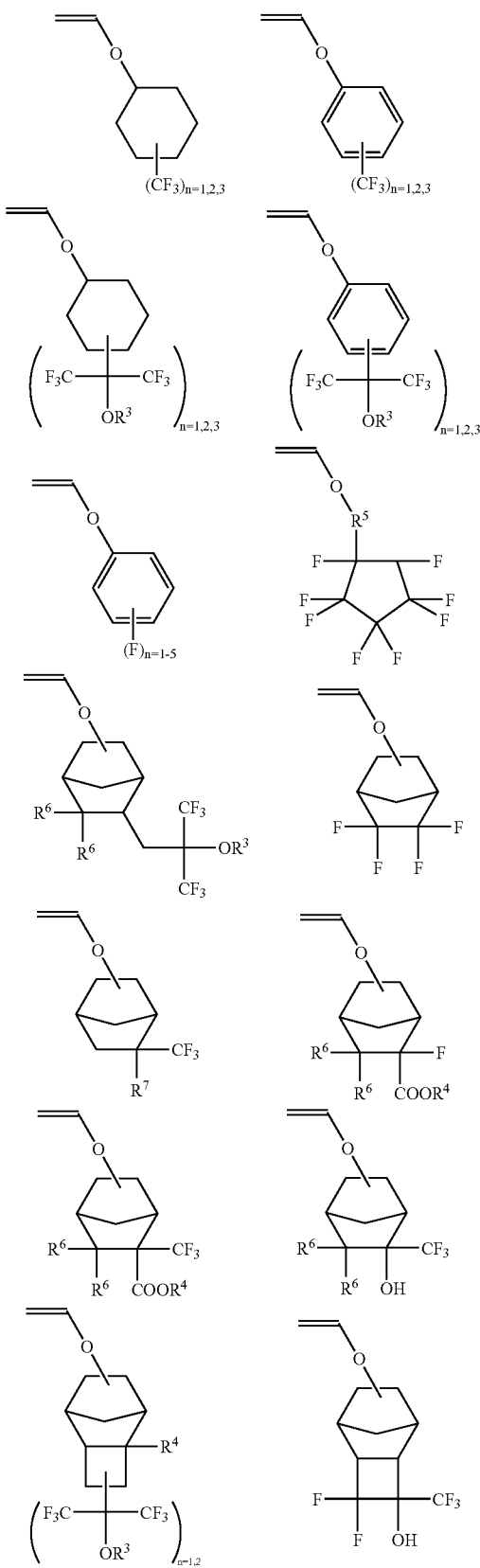

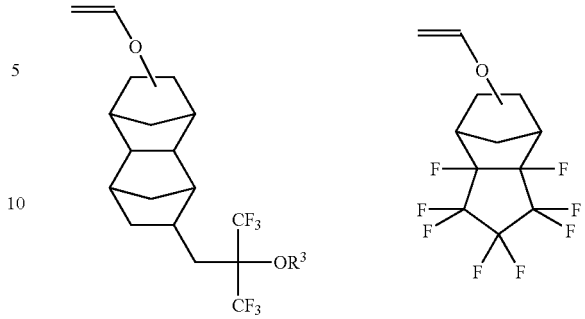

where $R^3$ is H or an acid-labile protecting group;

$R^4$ is H, a $C_1$-$C_{15}$ alkyl group, or a $C_1$-$C_{15}$ substituent having an ether bond;

$R^5$ is a $C_0$-$C_5$ alkyl group;

$R^6$ is H or F; and $R^7$ is $CF_3$, OH, $CO_2H$, $CO_2R^8$, or $OCOR^8$ where $R^8$ is $C_1$-$C_{15}$ alkyl group.

Of the fluorine-containing vinyl ethers represented by the above structural formulas, those containing a hexafluoroisopropanol unit (—C(CF$_3$)$_2$—OH) or hexafluoroisopropanol derivative unit (—C(CF$_3$)$_2$—OR$^3$, where $R^3$ is a hydrogen or acid-labile protecting group optionally containing a hetero atom(s) such as oxygen) serve to improve adhesion of the resulting polymer to substrate. Examples of such acid-labile protecting group include t-butoxycarbonyl group, methoxymethyl group, 2-methyl-2-adamantyl ester group, and 2-ethyl-2-adamantyl ester group. Of fluorine-containing vinyl ethers, those containing structures, such as bicyclo[2.2.1]heptane and tricyclodecane, are preferable since polymers derived from those vinyl ethers are low in light absorption caused by double bond and are superior in heat resistance.

It is possible to apply various known processes to produce the fluorine-containing vinyl ether of the present invention. For example, it is possible to treat a fluorine-containing alcohol with an alkali metal, followed by a reaction with acetylene or vinyl halide. As this alkali metal, it is possible to use various alkali metal compounds, such as sodium hydride, potassium hydride, sodium hydroxide, potassium hydroxide, and potassium carbonate.

It is known to synthesize vinyl ethers by vinyl exchange reaction using palladium as catalyst. This vinyl exchange reaction is conducted in the presence of a vinyl ether or alcohol to obtain the target vinyl ether. In particular, it is preferable to use a palladium catalyst, since reaction conditions become mild and since side reactions do not easily occur. It is possible to use a bivalent palladium such as palladium acetate Pd(OAc)$_2$ as the palladium catalyst. It is also possible to use a ligand (to be bonded to palladium) for the purpose of controlling the reaction activity of palladium. The type of this ligand is not particularly limited. Preferable examples of this ligand include nitrogen-containing bidentate ones (e.g., 2,2'-bipyridyl and 1,10-phenanthroline) since the amount of by-products is small. It is possible to react palladium with ligand prior to the vinyl exchange reaction. Alternatively, it is possible to separately add palladium and ligand to the reaction system upon the vinyl exchange reaction to make ligand bonded to palladium.

The invention claimed is:

1. A fluorine-containing vinyl ether, which is represented by the formula 2,

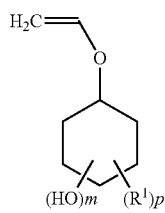

(2)

where $R^1$ is at least one substituent selected from the group consisting of —F, —$CF_3$, and —$R^2C(CF_3)_2OR^3$, where $R^2$ is $CH_2$ or $C_2H_4$, and $R^3$ is H or an acid-labile protecting group, and
p is an integer of 1-5, and m is 0 or 1.

2. A fluorine-containing vinyl ether, which is represented by the formula 3,

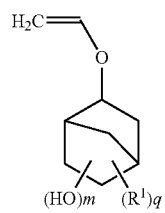

(3)

where $R^1$ is at least one substituent selected from the group consisting of —F, —$CF_3$, and —$R^2C(CF_3)2OR^3$, where $R^2$ is $CH_2$ or $C_2H_4$, and $R^3$ is H or an acid-labile protecting group, and
q is an integer of 1-4, and m is 0 or 1.

3. A fluorine-containing vinyl ether, which is represented by the formula 5,

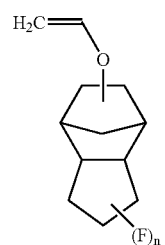

(5)

where n is an integer of 1-8.

4. A fluorine-containing vinyl ether, which is represented by the formula 6,

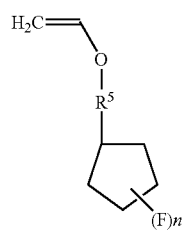

(6)

where $R^5$ is a $C_0$-$C_5$ alkyl group, and n is an integer of 1-8.

5. A fluorine-containing polymer comprising a unit derived from a fluorine-containing vinyl ether according to claim 1.

6. A resist composition comprising a fluorine-containing polymer according to claim 5.

7. A fluorine-containing copolymer comprising:
a first unit derived from a first monomer that is a fluorine-containing vinyl ether represented by the formula 8:

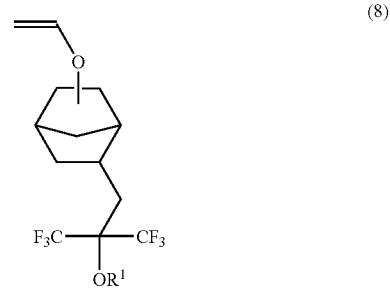

(8)

where $R^1$ is —H or a $C_1$-$C_8$ alkyl group that optionally contains an oxygen atom; and
a second unit derived from a second monomer that is at least one selected from the group consisting of acrylic esters and methacrylic esters.

8. A fluorine-containing copolymer according to claim 7, wherein the second monomer contains an acid-labile protecting group.

9. A fluorine-containing copolymer according to claim 7, wherein the second monomer is a first methacrylic ester represented by the general formula 9:

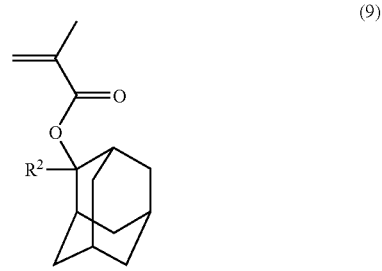

(9)

where $R^2$ is —$CH_3$ or —$CH_2CH_3$.

10. A fluorine-containing copolymer according to claim 7, wherein the second monomer is an acrylic or methacrylic ester comprising a lactone ring.

11. A fluorine-containing copolymer according to claim 7, wherein the second monomer is a second methacrylic ester represented by the formula 10:

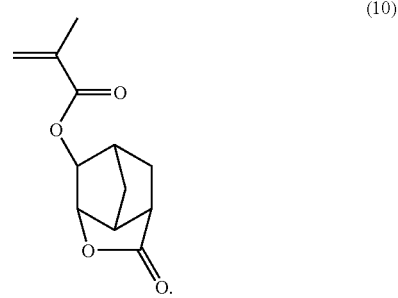

(10)

12. A fluorine-containing copolymer according to claim 7, wherein the second monomer is a combination of first and second methacrylic esters represented by the formulas 9 and 10, and wherein the fluorine-containing vinyl ether is represented by the formula 11,

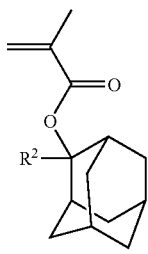
(9)

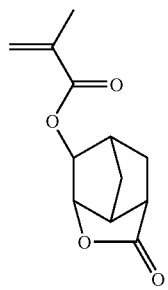
(10)

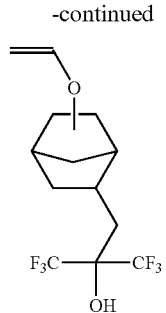
(11)

where $R^2$ is —$CH_3$ or —$CH_2CH_3$.

13. A resist composition comprising a fluorine-containing copolymer according to claim 7.

14. A fluorine-containing polymer comprising a unit derived from a fluorine-containing vinyl ether according to claim 2.

15. A resist composition comprising a fluorine-containing polymer according to claim 14.

16. A fluorine-containing polymer comprising a unit derived from a fluorine-containing vinyl ether according to claim 3.

17. A resist composition comprising a fluorine-containing polymer according to claim 16.

18. A fluorine-containing polymer comprising a unit derived from a fluorine-containing vinyl ether according to claim 4.

19. A resist composition comprising a fluorine-containing polymer according to claim 18.

* * * * *